United States Patent [19]

Hartman et al.

[11] Patent Number: 5,227,490

[45] Date of Patent: Jul. 13, 1993

[54] FIBRINOGEN RECEPTOR ANTAGONISTS

[75] Inventors: George D. Hartman, Lansdale; Wasyl Halczenko, Hatfield, both of Pa.

[73] Assignee: Merck & Co., Inc., Rahway, N.J.

[21] Appl. No.: 838,950

[22] Filed: Feb. 21, 1992

[51] Int. Cl.$^5$ .................. C07D 211/08; C07D 211/36; A61K 31/445

[52] U.S. Cl. .................... 514/317; 514/329; 514/330; 514/331; 546/224; 546/225; 546/229; 546/233; 546/237

[58] Field of Search ............... 546/225, 226, 237, 238, 546/224, 229, 233; 514/330, 317, 329, 331

[56] References Cited

U.S. PATENT DOCUMENTS

| | | | |
|---|---|---|---|
| 5,023,233 | 6/1991 | Nutt et al. | 514/11 |
| 5,037,808 | 8/1991 | Tjoeng et al. | 514/20 |

FOREIGN PATENT DOCUMENTS

| | | | |
|---|---|---|---|
| 0405537A1 | 1/1989 | European Pat. Off. | |
| 0341915 | 11/1989 | European Pat. Off. | 530/328 |
| 0352249A1 | 1/1990 | European Pat. Off. | |
| 0372486A2 | 6/1990 | European Pat. Off. | |
| 0381033A1 | 8/1990 | European Pat. Off. | |
| 0384362A2 | 8/1990 | European Pat. Off. | |
| 0445796A2 | 9/1991 | European Pat. Off. | 514/20 |
| 89/05150 | 6/1989 | World Int. Prop. O. | 530/324 |
| 90/02751 | 3/1990 | World Int. Prop. O. | 530/328 |
| 90/15620 | 12/1990 | World Int. Prop. O. | 530/328 |
| 91/01331 | 2/1991 | World Int. Prop. O. | 530/328 |
| 91/05562 | 5/1991 | World Int. Prop. O. | 530/328 |
| 91/11458 | 8/1991 | World Int. Prop. O. | 530/328 |
| 91/15515 | 10/1991 | World Int. Prop. O. | 530/328 |

*Primary Examiner*—C. Warren Ivy
*Assistant Examiner*—Phyllis G. Spivack
*Attorney, Agent, or Firm*—Charles M. Caruso; Richard S. Parr; Monte R. Browder

[57] ABSTRACT

Novel fibrinogen receptor antagonists of the formula

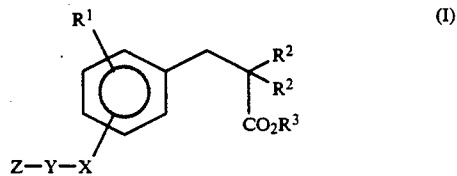

are provided in which the claimed compounds exhibit fibrinogen receptor antagonist activity, inhibit platelet aggregation and are therefore useful in modulating thrombus formation.

15 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigentically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between nonterminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., Proc. Nat'l Acad. Sci. U.S.A., 83, 5708–5712 (1986) explore a series of synehetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Haverstick et al., Blood 66(4), 946–952 (1985). Other inhibitors are disclosed in Eur. Pat. App. Nos. 275,748 and 298,820.

A number of low molecular weight polypeptide factors have been isolated from shake venom. These factors apparently have high affinity for the gpIIb/IIIa complex. For example, Huang et al., J. Biol Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. U.S.A., 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tri-peptide Arg-Gly-Asp has low activity. At present, there is little understanding of how other amino acids coupled to this sequence influence binding specificity. U.S. Pat. No. 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood.

The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$-A-(W)$_a$-X-(CH$_2$)$_b$-(Y)$_c$-B-Z-COOR wherein $R^1$ is a guanidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

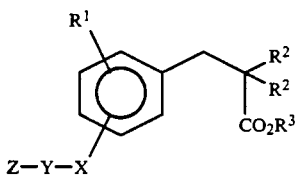

(I)

and the pharmaceutically acceptable salts thereof wherein:

$R^1$ is chosen independently from
  hydrogen,
  $C_{1-6}$ alkyl,
  aryl$C_{4-10}$alkyl,
  aryl,
  carboxy,
  $C_{1-6}$ alkyloxy,
  carboxy$C_{0-6}$alkyl,
  carboxy$C_{1-6}$alkyloxy,
  hydroxy$C_{0-6}$alkyl,
  $C_{1-4}$ alkylsulfonyl$C_{0-6}$alkyl,
  $C_{0-4}$ alkylamino$C_{0-6}$alkyl,
  aryl$C_{0-10}$alkylamino$C_{0-6}$alkyl,
  $C_{2-10}$ acylamino$C_{0-6}$alkyl,
  $C_{1-4}$ carboalkoxy$C_{0-6}$alkyl, or
  halogen;

$R^2$ is chosen independently from
  H,
  halogen,
  hydroxy,
  $C_{1-6}$ alkyloxy,
  aryl $C_{0-4}$ alkyl,
  aryl $C_{0-6}$ alkyloxy,
  $C_{1-6}$ alkyl, wherein the alkyl group is unsubstituted or substituted with one or more groups chosen from: (a) hydroxy, (b) $C_{1-4}$ alkyloxy, (c) amino $C_{0-10}$ alkylcarbonyl, (d) aryl$C_{0-10}$alkylcarbonyl, (e) $C_{1-6}$alkylcarbonylamino, (f) aryl$C_{0-4}$ alkylcarbonylamino, (g) $C_{1-6}$alkylsulfonyl, (h) aryl$C_{0-6}$alkylsulfonyl, (i) $C_{1-6}$ alkylsulfonylamino, (j) aryl$C_{0-10}$ alkylsulfonylamino, (k) $C_{1-10}$ alkyl oxycarbonylamino, (l) aryl$C_{0-6}$alkylamino, (m) aryl$C_{0-6}$ alkylcarbonylamino, (n) amino, (o) carboxyl, (p) aryl (q) -carbonyl-P or —SO$_2$-P where P is a single L or D amino acid or a sequence of 2–4 L or D amino acids connected by amide linkages.
  carboxyl,
  $C_{1-6}$ alkylcarbonyl,
  aryl $C_{0-10}$ alkylcarbonyl,
  $C_{1-6}$ alkyloxycarbonylamino$C_{1-6}$alkyl,
  $C_{0-6}$ alkylaminocarbonylamino$C_{1-6}$alkyl,
  aryl$C_{0-6}$alkylaminocarbonylamino$C_{1-6}$alkyl,
  aryl $C_{0-6}$alkyloxycarbonylamino$C_{1-6}$alkyl
  $C_{1-6}$ alkyloxycarbonyl, or
  aryl$C_{0-6}$alkyloxycarbonyl,
  and provided that when there is more than one $R^2$ on the same carbon atom, they may be the same or different;

$R^3$ is
  H,
  $C_{1-6}$ alkyl, or
  aryl$C_{1-10}$alkyl;

Z is
  $NR^4R^5$ wherein $R^4$ and $R^5$ are independently H, $C_{1-6}$ alkyl, aryl $C_{1-10}$ alkyl wherein said alkyl groups are unsubstituted or substituted with $C_{1-4}$ alkyloxy, carboxy $C_{0-6}$ alkyl, hydroxy, halogen, or
  a 4–9 membered mono or bicyclic ring system containing 1, 2 or 3 heteroatoms chosen from N, O or S and either unsubstituted or substituted with $R^4$ or $R^5$, or

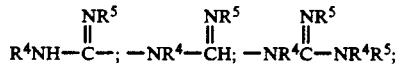

Y is
  $C_{1-10}$ alkyl either unsubstituted or substituted with one or more groups selected from $R^4$ or $R^5$;
  $C_{4-8}$ cycloalkyl,
  aryl,
  $C_{0-3}$alkylaryl$C_{0-3}$alkyl,
  $C_{0-3}$alkylaryl$C_{0-3}$alkylcarbonyl,
  $C_{0-3}$alkylaryl$C_{0-3}$alkylcarboxamido,
  $C_{0-3}$alkylaryloxy$C_{0-3}$alkyl,
  $C_{0-3}$alkyloxy$C_{0-6}$alkyl,

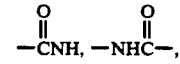

or
  —(CH$_2$)$_m$—Q—(CH)$_n$ where Q is a $C_{2-8}$ membered heterocyclic ring containing 1, 2, or 3 heteroatoms chosen from N, O or S and substituted or unsubstituted with oxo, thio, or $C_{1-4}$ alkyl and m and n are chosen from the integers 0, 1, 2, or 3;

X is
  O,
  S,
  SO,
  SO$_2$,
  CO,
  —NR$^4$CO—,
  —CONR$^4$—,
  —CH$_2$—,
  —CH=CH,
  —C≡C—,
  —NR$^4$CS—,

—CSNR$^4$—,
SO$_2$NR$^4$, or
NR$^4$SO$_2$.

A preferred group of compounds of the present invention are those defined for the general structure:

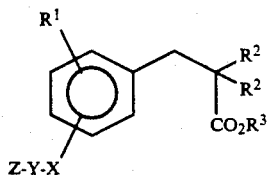

wherein:
R$^1$ is H,
C$_{1-3}$ alkyl, or
carboxyC$_{1-3}$alkyl;
R$^2$ is chosen from:
  hydroxy,
  halogen,
  hydrogen,
  arylC$_{0-4}$alkyl,
  carboxylC$_{0-2}$alkyl,
  C$_{1-6}$ alkyloxy carbonyl,
  C$_{1-6}$ alkyl, wherein the alkyl group is unsubstituted or substituted with C$_{1-6}$ alkylsulfonyl, C$_{1-6}$alkylsulfonylamino, C$_{1-6}$ alkylcarbonyl; arylC$_{0-6}$alkylamino, C$_{1-6}$ alkylcarbonylamino, arylC$_{0-6}$alkylsulfonyl, arylC$_{0-6}$alkylsulfonylamino, arylC$_{0-6}$alkylcarbonyl, or arylC$_{0-6}$ alkylcarbonylamino;
R$^3$ is
  H, or
  C$_{1-6}$ alkyl;
Z is
  NR$^4$R$^5$, or
  a 4-9 membered mono or bicyclic ring system containing 1 or 2 heteroatoms chosen from N and either unsubstituted or substituted with R$^4$ or R$^5$, or

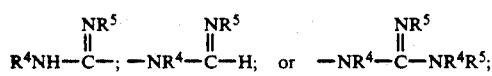

Y is
  C$_{1-10}$ alkyl either unsubstituted or substituted with R$^4$ or R$^5$,
  —CH$_2$arylCH$_2$—,
  —CH$_2$arylCO—, or
  —CH$_2$arylOCH$_2$—;
X is
  —O—,
  —S—,
  —SO—,
  —SO$_2$—,
  —CO—
  —NR$^4$CO—,
  —CONR$^4$—,
  —CH$_2$—,
  —CH=CH—, or
  —C≡C—.

A more preferred group of compounds of the present invention are those defined for the general structure:

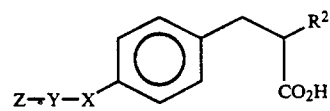

wherein,
R$^2$ is chosen from:
  hydrogen,
  hydroxy,
  halogen,
  C$_{1-6}$ alkyloxycarbonyl,
  carboxy
  C$_{1-6}$ alkyl, wherein the alkyl group is substituted with
    C$_{1-6}$ alkylsulfonyl,
    arylC$_{0-6}$alkylsulfonyl,
    C$_{1-6}$ alkylsulfonylamino,
    arylC$_{0-6}$alkylsulfonylamino,
    C$_{1-6}$ alkylcarbonyl,
    arylC$_{1-6}$alkylcarbonyl,
    C$_{1-6}$ alkylcarbonylamino
    arylC$_{0-6}$alkylcarbonylamino,
    amino, or
    aryl;
Z is
  NR$^4$R$^5$ or
  a 5-7 membered monocyclic ring system containing 1 or 2 heteroatoms chosen from N and either unsubstituted or substituted with R$^4$ or R$^5$; or

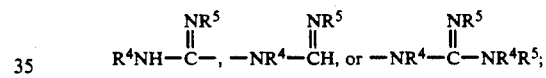

Y is
  C$_{1-6}$ alkyl either unsubstituted or substituted with R$^4$ or R$^5$;
  —CH$_2$arylCH$_2$—, or
  —CH$_2$arylCO—;
X is
  —O—,
  —SO$_2$,
  —NR$^4$CO—,
  —CONR$^4$—,
  —CH$_2$—,
  —CO—, or
  —CH=CH—.

DETAILED DESCRIPTION OF THE INVENTION

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, sisulfate, sitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" shall include aspirin and dipyridamole.

The term "aryl" shall mean a mono- or polycyclic system composed of 5- and 6-membered aromatic rings containing 0, 1, 2, 3, or 4 heteroatoms chosen from N, O or S and either unsubstituted or substituted with $R^4$ or $R^5$.

The term "alkyl" shall mean straight or branched alkane, alkene or alkyne. The term "alkoxy" shall be taken to include an alkyl portion where alkyl is as defined above.

The terms "arylalkyl" and "alkylaryl" shall be taken to include an alkyl portion where alkyl is as defined above and to include an aryl portion where aryl is as defined above. The $C_{0-n}$ or $C_{1-n}$ designation where n may be an integer from 1-10 or 2-10 respectively refers to the alkyl component of the arylalkyl or alkylaryl unit.

The term "halogen" shall include fluorine, chlorine, iodine and bromine.

The term "oxy" shall mean an oxygen (O) atom. The term "thio" shall mean a sulfur (S) atom. Under standard nonmenclature used throughout this disclosure, the terminal portion of the designated side chain is described first followed by the adjacent functionallity toward the point of attachment. For example, a $C_{1-6}$ alkyl substituted with $C_{1-6}$ alkylcarbonylamino is equivalent to

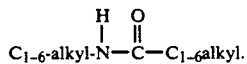

In the schemes and examples below, various reagent symbols have the following meanings:
BOC(Boc): t-butyloxycarbonyl.
Pd-C: Palladium on activated carbon catalyst.
DMF: Dimethylformamide.
DMSO: Dimethylsulfoxide.
CBZ: Carbobenzyloxy.
$CH_2Cl_2$: Methylene chloride.
$CHCl_3$: chloroform.
EtOH: ethanol.
MeOH: methanol.
EtOAc: ethyl acetate.
HOAc: acetic acid.
BOP: Benzotriazol-1-yloxytris(dimethylamino)phosphonium, hexafluorophosphate.
EDC: 1-(3-Dimethylaminopropyl)-3-ethylcarbodiimide
Oxone: potassium peroxymonosulfate
LDA: Lithium diisopropylamide The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., *Amer. J. Physiol.*, 252(H), 615-621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 1.0-100 mg/kg/day and most preferably 1-20 mg/kg/day. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittant throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylkcellulose, polyethylene glycol, waxes and the like. Lubricants used in these dosage forms include sodium oleate, sodium sterate, magnesium sterate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug cariers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-coagulation agents or thrombolytic agents such as plasminogen activators or streptokinase to achieve synergystic effects in the treatment of various vascular pathologies. They may also be combined with heparin, aspirin, or warfarin.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2 B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 μM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Synthesis of Novel Fibrinogen Receptor Antagonists:

Compounds useful as fibrinogen receptor antagonists may be prepared according to the general scheme depicted in Scheme 1.

In general terms, a halophenol (1-1) is reacted with sodium hydride and the resulting sodium salt is treated with the BOC-protected-4-piperidinyl butylbromide derivative(1-2) to yield an ether derivative(1-3). This product is subsequently reacted with n-butyl lithium and tributyl tin chloride to yield the stannane intermediate(1-4). This product is then reacted with 2-bromomethyl acrylate to yield the 1,4-substituted aromatic piperidinyl derivative (1-5). n-Butyl mercaptan is then added to the activated double bond to yield the sulfur substituted compound (1-6) which is subsequently oxidized to the sulfone (1-7). Deprotection of the carboxyl and piperidine groups then provides the sulfone acid (1-8).

Scheme 1

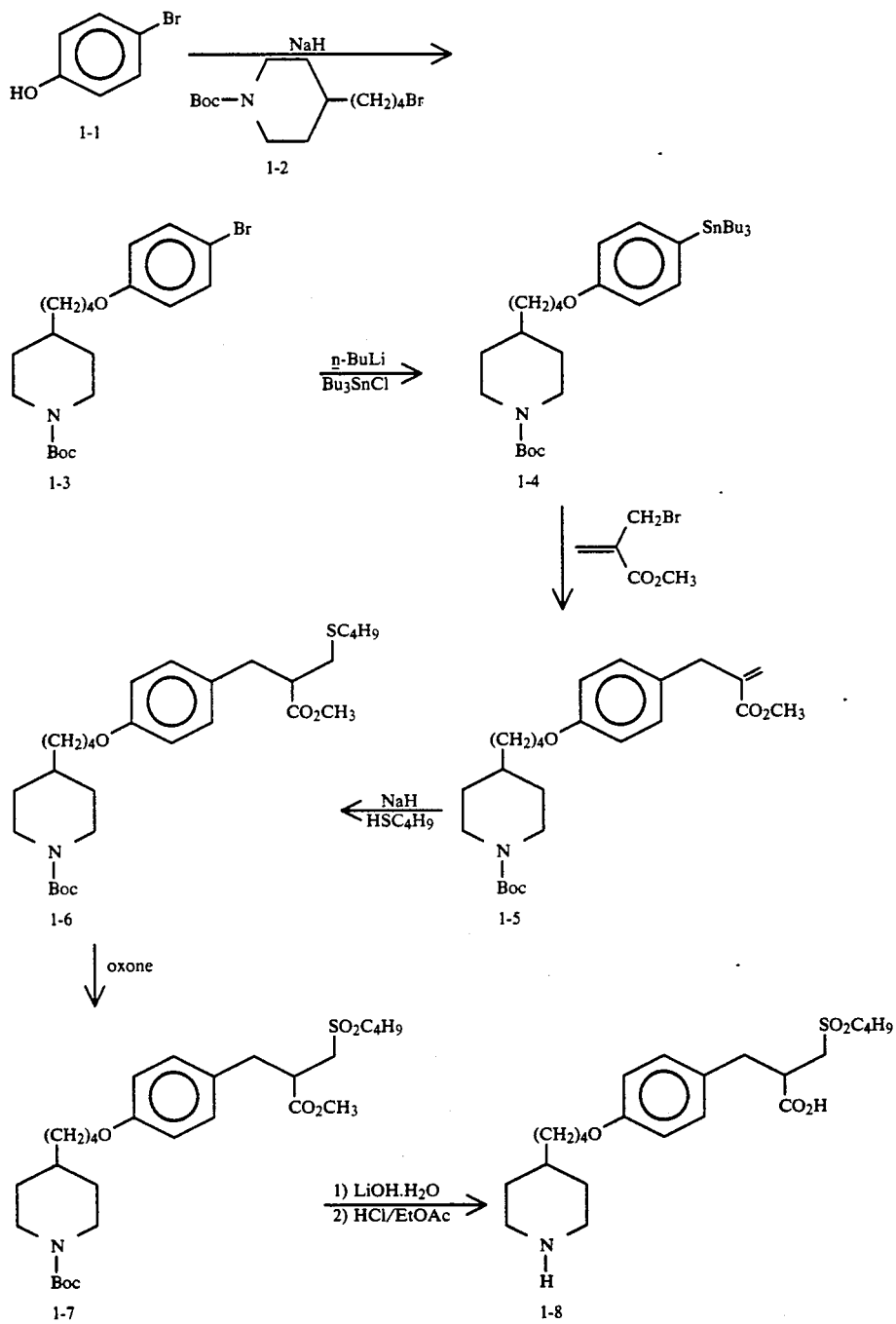

Compounds claimed in the instant invention and depicted in the following formula:

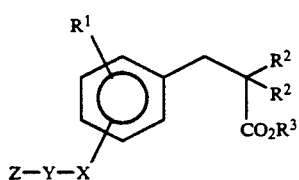

(I)

can readily be prepared according to this general scheme by substituting or replacing the various reagents in Scheme 1.

For example, a trisubstituted 4-halophenol derivative wherein the 3rd substituent ($R^1$) may be $C_{1-6}$ alkyl, aryl$C_{1-10}$alkyl, aryl, carboxy, $C_{1-6}$ alkyloxy, carboxy$C_{1-6}$alkyl, carboxy$C_{1-6}$alkyloxy, hydroxy$C_{1-6}$alkyl, $C_{1-4}$ alkylsulfonyl$C_{1-6}$alkyl, $C_{0-4}$ alkylamino$C_{1-6}$alkyl, $C_{0-10}$ arylalkylamino$C_{1-6}$alkyl, $C_{2-10}$ acylamino, $C_{1-6}$ alkyl, $C_{1-4}$ carboalkoxy$C_{1-6}$alkyl or halogen may be used as the initial reactant. A 4-halophenol compound or a trisubstituted ($R^1$) derivative may then be reacted with (1-2) or another suitably substituted alkyl halide to yield a compound of the general formula (II):

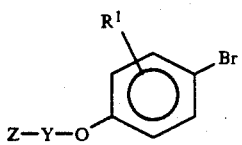

wherein Z-Y-hal is a suitably substituted alkyl halide and Z is chosen from amines or substituted amines such as $NR^4R^5$ wherein $R^4$ and $R^5$ are independently H, $C_{1-6}$ alkyl, aryl$C_{1-10}$alkyl wherein the alkyl groups may be unsubstituted or substituted with $C_{1-4}$ alkyloxy, carboxy$C_{0-6}$alkyl, hydroxy, or halogen. Z may also be a 4–9 membered mono or bicyclic ring system containing 1, 2 or 3 heteroatoms chosen from N, O or S and either unsubstituted or substituted with $R^4$ or $R^5$. In addition Z may be

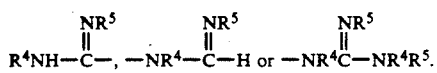

The Y component which is covalently bonded to Z may be $C_{1-10}$ alkyl either unsubstituted or substituted with one or more groups selected from $R^4$ or $R^5$, $C_{4-8}$ cycloalkyl, $C_{0-3}$ alkylaryl$C_{0-3}$alkyl, $C_{0-3}$ alkylaryl$C_{0-3}$alkylcarbonyl, $C_{0-3}$ alkylaryl$C_{0-3}$alkylcarboxamido, $C_{0-3}$ alkylaryloxy$C_{0-3}$alkyl, $C_{0-3}$ alkyloxy$C_{0-6}$alkyl,

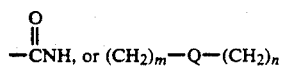

where Q is a $C_{2-8}$ heterocyclic ring containing 1, 2 or 3 heteratoms chosen from N, O, or S and substituted or unsubstituted with oxo, thio, or $C_{1-4}$ alkyl and m and n are chosen from the integers 0, 1, 2, or 3; or aryl. The Y constituent contains the reactive halide which is amenable to substitution by a nucleophilic di- or trisubstituted 4-halophenol compound.

The generic compound depicted in formula (II) may then be reacted with n-butyl lithium and a trisubstituted tin chloride to yield 1-4 or other suitable stannane intermediate. This is then reacted with 2-bromomethyl acrylate to yield a compound of the general formula (III):

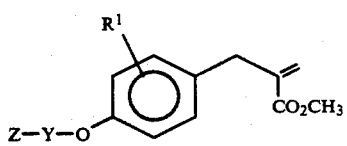

1-5 is a representative example of a compound within the structure depicted in formula (III). The compounds within formula (III) contain an activated double bond which is amenable to further elaboration. For example, n-butyl mercaptan or other suitable reagents such as: sodium methoxide, benzyl mercaptan, benzylamine, or other suitable amine can be reacted with (III) to form a compound with the general formula (IV) wherein the $R^{2'}$ group represents the nucleophile. If $R^{2'}$ is an alkyl or benzyl mercaptan group it can be further oxidized to the sulfone or sulfoxide derivative. If $R^{2'}$ is a benzylamine, after addition to the activated double bond it can be reduced to the free amine and further reacted with benzoyl chloride, alkylsulfonyl chloride or aryl$C_{0-10}$alkylsulfonyl chloride to yield compounds of the claimed invention.

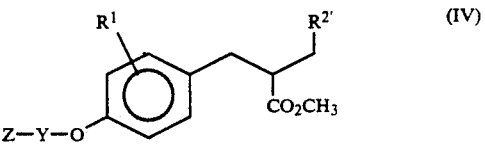

The methyl ester group of IV may readily be substituted with another $C_{1-6}$ alkyl constituent, an aryl$C_{1-10}$alkyl constituent, or hydrogen to yield compounds of the general formula (V):

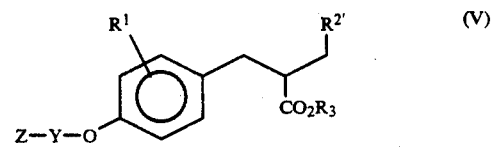

EXAMPLE 1

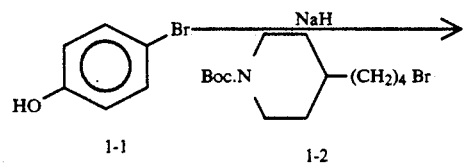

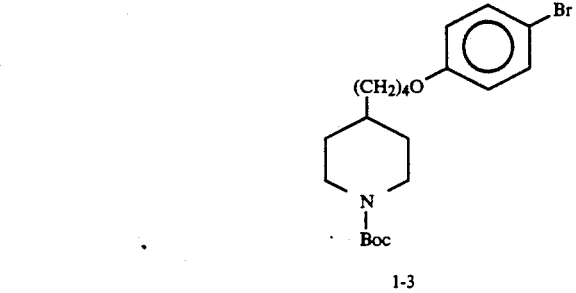

4-[4-(N-t-Butyloxycarbonylpiperidin-4-yl)butyloxy]-bromobenzene (1-3)

A solution of 1-1 (2.0 g, 11.43 mmoles) in 20 ml DMF was added at 0°–5° C. to sodium hydride (NaH) (0.27 g, 11.5 mmoles) suspended in DMF (10 ml) and this was stirred for 1 hour to give a clear, dark solution. 4-(4-N-t-butyloxycarbonylpiperidinyl)butyl bromide (1-2) (3.68 g, 11.5 mmoles) in 4 ml DMF was then added dropwise at 0°–10° C. with stirring. 1-2 was prepared by first reacting 4-piperidine-2-ethanol (available from American Tokyo Kasec) (130 g, 1.0 mole) with 3N NaOH (336 mL, 1.0 mole) at 0° C. and di-t-butylcarbonate (221.8 g, 1.0 mole). This Boc-protected piperidine (102.5 g, 0.45 m) was then reacted with oxayl chloride (55.8 ml, 0.64 mole); DMSO (54.2 ml, 0.76 mole) and $NEt_3$ (213 ml, 1.53 mole). The resultant aldehyde was reacted with carbomethoxytriphenylphosphorane (179 g, 0.536 mole) to give a trans methyl ester which was reduced ($H_2$/Pd), hydrolyzed (NaOH), reduced ($BH_3$) and brominated ($(C_6H_5)_3P$, $CBr_4$) to give (1-2). The reaction between 1-1 and 1-2 was allowed to proceed for 16 hours as the temperature slowly rose to ambient temperature or 25° C. The solvent was removed under vaccum at less than 30° C. and the resultant residue was taken up in 10% aqueous potassium hydrogen sulfate (KHSO$_4$) solution (500 ml) and extracted with ether (Et$_2$O). The ether extract was washed with H$_2$O, and brine, and then dried with sodium sulfate (Na$_2$SO$_4$). The solvent was then removed. The residue was purified by flash chromatography on silica gel eluting with hexane/ethyl acetate (EtOAc) in a 1 1/2 ratio to yield pure 1-3 as an oil.

$^1$H NMR (300 MHz, CDCl$_3$) δ1.04(2H,m), 1.20–1.42 (3H,m), 1.47 (9H,s), 1.68 (2H,d), 1.76 (2H,m), 2.68 (2H,t), 3.91 (2H,t), 4.09(2H,m), 6.77 (2H,d), 7.36 (2H,d).

EXAMPLE 2

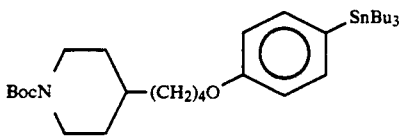

4-[4-(N-t-Butyloxycarbonylpiperidin-4-yl)butyloxy]-phenyltributyl stannane (1-4)

A solution of 1-3 (6.97 g, 17.5 mmoles) in THF (150 ml) was cooled to −75° C. and treated with n-butyl lithium (n-BuLi)(17.5 mmoles) dropwise. After stirring at −70° C. for 1 hr, tributyltin chloride (5.70 g, 17.5 mmol) was added dropwise. This was stirred at −70° C. for 2 hours and then overnight as the temperature was allowed to rise to ambient temperature. The solvent was subsequently removed and the residue was taken up in ether (500 ml), washed with H$_2$O and brine, and dried with Na$_2$SO$_4$. Solvent removal gave 1-4 as a viscous oil.

$^1$H NMR (300 MHz, CDCl$_3$) δ0.88 (9H, t), 1.0–1.15 (8H, m), 1.26–1.40 (6H, m), 1.47 (9H, s), 1.48–1.55 (6H, m), 1.65 (2H, m), 1.78 (2H, m), 2.67 (2H, bt), 3.94 (2H, t), 4.06 (2H, m), 6.99 (2H, d), 7.35 (2H, d).

EXAMPLE 3

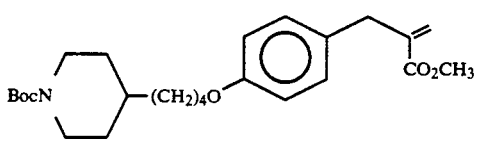

Methyl
2-[4-(4-N-t-Butyloxycarbonylpiperidin-4-yl)butyloxy]-phenylmethyl propenoate (1-5)

To a solution of bis(dibenzylideneacetone) palladium (0.03 g, 0.067 mmoles) in tetrahydrofuran (THF) (5 ml) was added triphenylphosphine (0.035 g, 0.134 mmoles), followed by addition of methyl-2-bromomethyl acrylate (0.40 g, 2.24 mmol) and 1-4 (1.48 g, 2.24 mmoles). The reaction solution was flushed with nitrogen (N$_2$), stoppered, and heated at 50° C. for 48 hours. The cooled reaction mixture was then poured into a mixture of ether (100 ml) and water (100 ml) containing 1.5 g of sodium floride (NaF). The organic phase was washed with brine, dried (Na$_2$SO$_4$) and the solvent removed. The residue was purified by flash chromatography on silica gel eluting with hexane/EtOAc in a 9/1 ratio to give pure 1-5.

$^1$H NMR (300 MHz, CDCl$_3$) δ1.10 (2H, m), 1.24–1.40 (4H, m), 1.45 (9H, s), 1,65 (2H, m), 1.74 (2H, m), 2,68 (2H, bt), 3.68 (3H, s), 3.73 (3H, s), 3.92 (2H, t), 4.07 (2H, m), 5.93 (1H, m), 6.20 (1H, m), 6.80 (2H, d), 7.09 (2H, d).

EXAMPLE 4

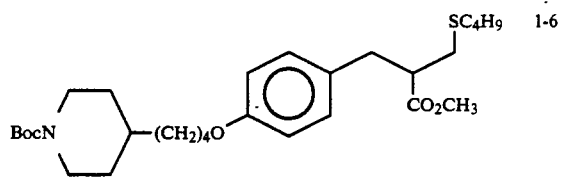

Methyl
2-[4-(4-N-t-Butyloxycarbonylpiperidin-4-yl)butyloxy]-phenylmethyl-3-(n-butylthio)propanoate (1-6)

To a solution of 1-5 (0.302 g, 0.7 mmoles) in MeOH (8 ml) was added n-butylmercaptan (0.063 g, 0.7 mmoles) at 0°–5° followed by a catalytic amount of NaH. This was stirred at 0°–5° for 1 hour and then at room temperature for 16 hours.

The solvent was removed in vacuo to give 1-6 as a viscous oil.

$^1$H NMR (300 MHz, CDCl$_3$) δ0.90 (3H, t), 1.09 (2H, m), 1.34–1.45 (3H, m), 1.46 (9H, s), 1.51 (2H, m), 1.66 (2H, d), 1.75 (2H, m), 2.49 (2H, t), 2.60–2095 (8H, m), 3.64 (3H, s), 3.92 (2H, t), 4.07 (2H, m), 6.70 (2H, d), 7.06 (2H, d).

EXAMPLE 5

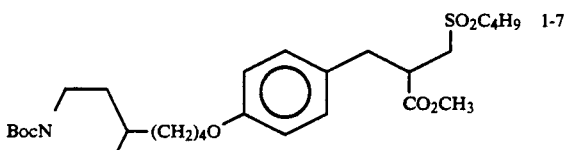

Methyl
2-[4-(4-N-t-Butyloxycarbonylpiperidin-4-yl)butyloxy]-phenylmethyl-3-(n-butylsulfonyl)propanoate (1-7)

A solution of 1-6 (0.7 mmoles) in MeOH (8 ml) was treated with 1.5 ml 2N H$_2$SO$_4$ solution at 0°–10° and then oxone (1.29 g, 21.0 mmoles) was added at 0°–10°. The resulting solution was stirred for 16 hours.

The reaction was diluted with 100 ml H$_2$O and extracted in CH$_2$Cl$_2$. The organic extract was washed with brine, dried (Na$_2$SO$_4$) and the solvent was removed. The residue was purified by flash chromtography on silica gel eluting with hexane/EtOAc (7:3) to give 1-7 as an oil.

$^1$H NMR (300 MHz, CDCl$_3$) δ0.92 (3H, t), 1.11 (2H, m), 1.13–1.45 (3H, m), 1.46 (9H, s), 1.62–182 (4H, m), 2.67 (2H, bt), 2.80–3.12 (5H, m), 3.29 (1H, m), 3.45 (1H, m), 3.70 (3H, s), 3.92 (2H, t), 4.08 (3H, m).

EXAMPLE 6

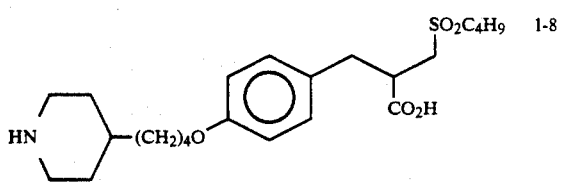

2-[4-(4-Piperidin-4-yl)butyloxy]phenylmethyl-3-(n-butylsulfonyl)propanoic acid (1-8)

A solution of 1-7 (0.31 g, 0.56 mmoles) in THF/MeOH/H$_2$O 1:1:1 (15 ml) was treated with LiOH.H$_2$O (0.067 g, 1.6 mmoles) at room temperature for 16 hours. The reaction mixture was then diluted with H$_2$O (100 ml), acidified with 10% KHSO$_4$ solution and extracted with EtOAc. The organic extract was washed in brine, dried (Na$_2$SO$_4$) and the solvent removed. The residue was purified by flash chromatography on silica gel eluting with CHCl$_3$/MeOH/HOAc 97:3:1 to give the desired acid.

$^1$H NMR (300 MHz, CDCl$_3$) δ0.91 (3H, t), 1.08 (2H, m), 1.25–1.4 (3H, m), 1.47 (9H, s), 1.67 (3H, m), 1.75 (3H, m), 2.66 (2H, bt), 2.85–3.00 (3H, m), 3.13 (1H, dd), 3.32 (1H, m), 3.45 (1H, m), 3.92 (2H, t), 4.03 (2H, m), 6.82 (2H, d), 7.01 (2H, d).

This acid (0.058 g) was dissolved in EtOAc (30 ml) and the solution was cooled to −30° and treated with HCl for 0.5 hour. The flask was then stoppered and the contents stirred at 0° for 1 hour.

The solvent was removed and the residue triturated with Et$_2$O to give pure 1-8.

$^1$H NMR (300 MHz, CD$_3$OD) δ0.94 (3H, t), 1.40 (4H, m), 1.50–1.81 (4H, m), 1.95 (2H, bd), 2.84 (1H, m), 3.00 (4H, m), 3.16 (1H, m), 3.30 (2H, m), 3.35 (2H, bd), 3.52 (1H, m), 3.96 (2H, t), 6.85 (2H, d), 7.15 (2H, d).

EXAMPLE 7

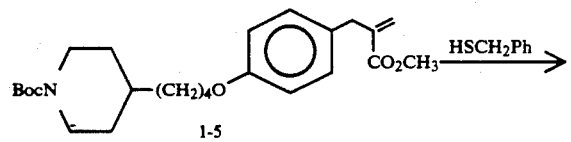

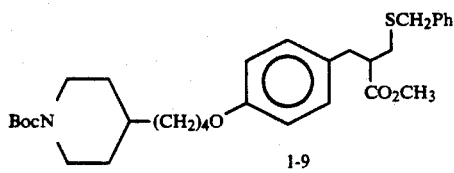

Methyl 2-[4-(4-N-t-Butyloxycarbonylpiperidin-4-yl)butyloxy]-phenylmethyl-3-(benzylthio)propanoate (1-9)

1-5 (0.432 g, 1.0 mmoles) was treated with benzylmercaptan (0.124 g, 1.0 mmole) as described for 1-6. Crude 1-9 had R$_f$ 0.45, silica gel, hexane/EtOAc (8:2).

EXAMPLE 8

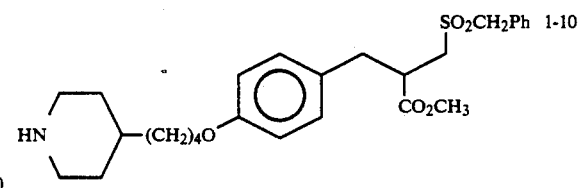

Methyl 2-[4-(4-Piperidin-4-yl)butyloxy]phenylmethyl-3-(benzylsulfonyl)propanoate (1-10)

A methanol solution (10 ml) of 1-9 (1.0 mmoles) was acidified at 0°–5° with 2 drops 2N H$_2$SO$_4$ solution and then oxone (3.0 mmoles) was added at 0°–5° with stirring. After 24 hours stirring the reaction mixture was diluted with H$_2$O and extracted with CH$_2$Cl$_2$. The organic extract was washed in H$_2$O, brine, dried (Na$_2$SO$_4$) and the solvent removed. The residue was purified by flash chromatography on silica gel eluting with hexane/EtOAc (75:25) to give pure 1-10 as an oil.

$^1$H NMR (300 MHz, CDCl$_3$) δ1.10 (2H, m), 1.25–1.45 (3H, m), 1.47 (9H, s), 1.65 (2H, d), 1.74 (2H, m), 2.61–2.92 (5H, m), 3.00 (1H, m), 3.21 (1H, m), 3.36 (1H, m), 3.70 (3H, s), 3.92 (2H, t), 4.06 (2H, m), 4.17 (2H, d), 6.70 (2H, d), 6.97 (2H, d), 7.25–7.40 (5H, m).

EXAMPLE 9

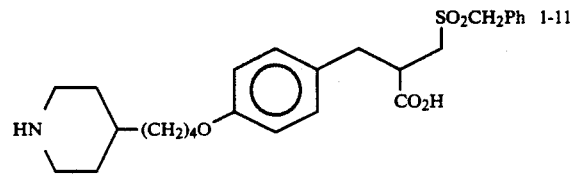

2-[4-(4-N-piperidin-4-ylbutyloxy]phenylmethyl]-3-(benzylsulfonyl)propanoic acid (1-11)

1-10 (0.2 g, 0.34 mmoles) was hydrolyzed with LiOH.H$_2$O (0.015 g, 0.35 mmoles) as described for 1-8 to provide the desired acid, R$_f$ 0.35 (silica gel, CHCl$_3$/MeOH/HOAc (97:3:1).

$^1$H NMR (300 MHz, CDCl$_3$) δ1.09 (2H, m), 1.25–1.45 (4H, m), 1.47 (9H, s), 1.65 (2H, d), 1.74 (2H, m), 2.64 (2H, bt), 2.78–2.95 (2H, m), 3.06 (1H, m), 3.12 (1H, m), 3.35 (1H, m), 3.92 (2H, t), 4.03 (2H, m), 0.419 (2H, s), 6.80 (2H, d), 7.02 (2H, d), 7.28 (2H, m), 7.35 (3H, m).

This acid was treated with HCl as described for 1-8 to provide crude 1-11. This was triturated to give 1-11 as a white solid.

$^1$H NMR (300 MHz, CD$_3$OD) δ1.36 (4H, m), 1.56 (3H, m), 1.76 (2H, m), 1.95 (2H, d), 2.81 (1H, m) 2,97 (4H, m), 3.15 (1H, bs), 3.36 (4H, m), 3.97 (2H, t), 4.34 (2H, s), 6.82 (2H, d), 7.07 (2H, d), 7.23 (5H, m).

EXAMPLE 10

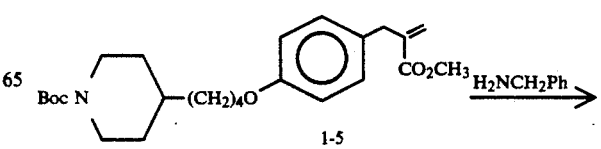

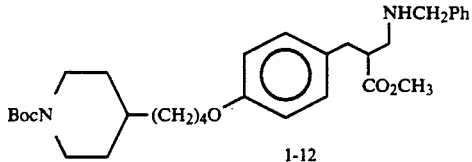

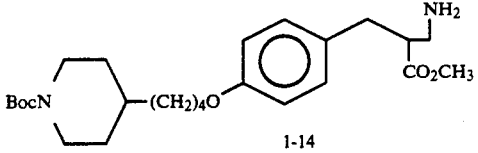

Methyl
2-[4-(4-N-t-Butyloxycarbonylpiperidin-4-yl)butyloxy]-phenylmethyl-3-(benzylamino)propanoate (1-12)

A solution of 1-5 (0.216 g, 0.5 mmoles) in toluene (8 ml) was treated with benzylamine (10 mmoles) and the resulting solution was heated at 100° for 16 hrs.

The reaction was diluted with EtOAC (100 ml) and this was washed with 10% KHSO$_4$ solution, H$_2$O, brine, and dried (Na$_2$SO$_4$). Solvent removal gave an oil that was purified by flash chromatography on silica gel eluting in CHCl$_3$/MeOH (98:2) to give 1-12 as an oil, R$_f$ 0.35 (silica gel, hexane/acetone (8:2).

$^1$H NMR (300 MHz, CDCl$_3$) δ1.09 (4H, m) 1.25–1.45 (4H, m), 1.47 (9H, s), 1.67 (2H, d), 1.76 (2H, m), 2.63–2.95 (8H, m), 3.63 (3H, s), 3.77 (1H, d), 3.91 (2H, t), 4.06 (2H, m), 6.76 (2H, d), 7.02 (2H, d), 7.23 (5H, m).

EXAMPLE 11

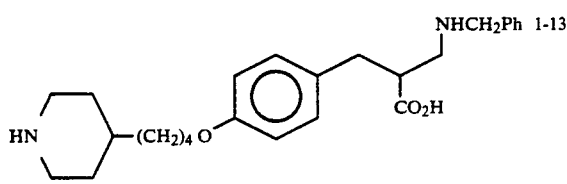

2-[4-(4-Piperidin-4-yl)butyloxy]phenylmethyl-3-(benzylamino)propanoic acid (1-13)

1-12(0.23 g, 0.43 mmoles) was treated with LiOH.H$_2$O (0.03 g, 0715 mmoles) as described for 1-8 to give the desired acid (1-13).

$^1$H NMR (300 MHz, CD$_3$OD) δ1.09 (2H, m) 1.34 (2H, m), 1.45 (9H, s), 1.51 (2H, m), 1.65–1.80 (4H, m), 2.72 (3H, m), 2.93 (2H, m), 3.10 (2H, m), 3.92 (2H, t), 4.05 (2H, d), 4.16 (2H, d), 6.81 (2H, d), 7.09 (2H, d), 7.40 (4H, m).

This acid was dissolved in EtOAc and treated with HCL gas as described for 1-8 to give 1-13 as a white solid after trituration with Et$_2$O.

$^1$H NMR (300 MHz, CD$_3$OD) δ1.40 (4H, m) 1.45–1.65 (3H, m), 1.69 (2H, m), 1.97 (2H, bd), 2.80 (1H, m), 3.00 (6H, m), 3.19 (1H, m), 3.35 (3H, m), 3.93 (2H, m), 4.18 (2H, m), 6.81 (2H, d), 7.08 (2H, d), 7.39 (5H, m).

EXAMPLE 12

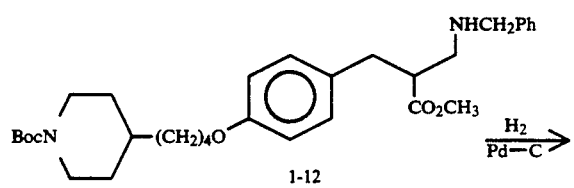

Methyl
2-[4-(4-N-t-Butyloxycarbonylpiperidin-4-yl)butyloxy]-phenylmethyl-3-(amino)propanoate (1-13)

A solution of 1-12 (0.80 g) in EtOH (30 ml) was treated with Pd(OH)$_2$/C (1.0 g) and this suspension was hydrogenated at atmospheric pressure. After 16 hours the solvent was removed and the residue was purified by flash chromatography on silica gel eluting with CHCl$_3$/MeOH(95:5) to give pure 1-14.

$^1$H NMR (300 MHz, CDCl$_3$) δ1.09 (2H, m) 1.23–1.44 (3H, m), 1.47 (9H, s), 1.65 (2H, d), 1.73 (2H, m), 2.15 (2H, bs), 2.59–2.80 (4H, m), 3.90 (2H, m), 3.65 (3H, s), 3.91 (2H, t), 4.04 (2H, m), 6.78 (2H, d), 7.06 (2H, d).

EXAMPLE 13

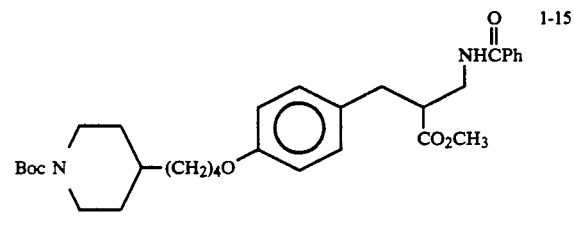

Methyl
2-[4-(4-N-t-Butyloxycarbonylpiperidin-4-yl)butyloxy]-phenylmethyl-3-(benzoylamino)propanoate (1-13)

A solution of 1-14 (0.2 g 0.45 mmoles) in CH$_2$Cl$_2$ at 0°–5° was treated with triethylamine (0.068 g, 0.67 mmoles) followed by benzoylchloride (0.07 g, 0.5 mmoles) and the resulting mixture was stirred at room temperature for 16 hours.

The solvent was removed and the residue was taken up in Et$_2$O (125 ml) and this was washed with H$_2$O, brine and dried (Na$_2$SO$_4$). Solvent removal gave a residue that was purified by flash chromatography on silica gel eluting with hexane/acetone (75:25) to give pure 1-15.

1H NMR (300 MHz, CDCl$_3$) δ1.09 (2H, m) 1.22–1.45 (3H, m), 1.49 (9H, s), 1.68 (2H, d), 1.74 (2H, m), 1.81 (2H, bs), 2.57 (2H, dt), 2.84 (1H, m), 3.00 (1H, m), 3.58 (1H, m), 3.68 (3H, s), 3.90 (2H, t), 4.07 (2H, d), 6.80 (2H, d), 7.10 (2H, d), 7.41 (3H, m), 7.70 (2H, m).

EXAMPLE 14

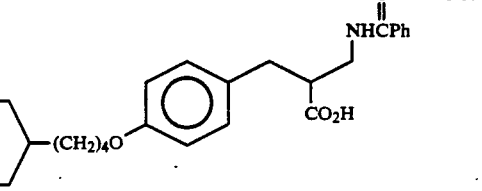

2-[4-(4-Piperidin-4-yl)butyloxy]phenylmethyl-3-(benzoylamino)propanoic acid (1-16)

1-15 (0.19 g 3.44 mmoles) was hydrolyzed with LiOH.H$_2$O as described for 1-8 to give the desired acid.

$^1$H NMR (300 MHz, CDCl$_3$) δ1.06 (2H, m) 1.25–1.45 (3H, m), 1.47 (9H, s), 1.63 (2H, d), 1.73 (2H, m), 2.65 (2H, bt), 2.84 (1H, m), 3.03 (2H, m), 3.58 (1H, m), 3.73 (1H, m), 3.90 (2H, t), 4.03 (2H, bd), 6.80 (2H, d), 7.12 (2H, d), 7.40 (3H, m), 7.69 (2H, d).

This acid was treated with HCl gas in EtOAc as described for 1-8 to give 1-16 as a white solid.

$^1$H NMR (300 MHz, CD$_3$OD) δ1.03–1.18 (2H, m) 1.22–1.53 (5H, m), 1.70 (2H, m), 2.52 (2H, m), 2.64–2.81 (2H, m), 2.95 (2H, m), 3.91 (2H, t), 6.78 (2H, d), 7.14 (2H, d), 7.44 (3H, m), 7.74 (2H, d).

EXAMPLE 15

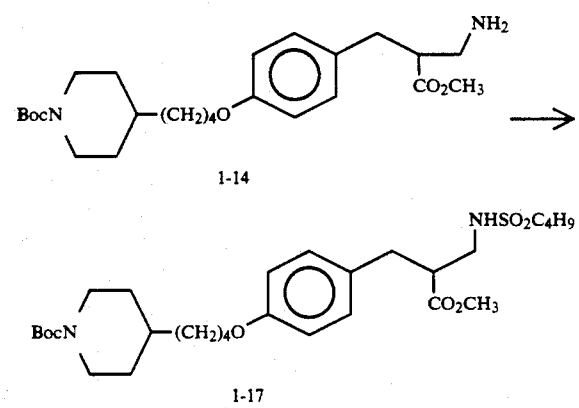

Methyl 2-[4-(4-N-t-Butyloxycarbonylpiperidin-4-yl)butyloxy]phenylmethyl-3-(n-butylsulfonylamino)propanoate (1-17)

A solution of 1-14 (0.2 g, 0.45 mmoles) in acetonitrile (10 ml) was treated with butanesulfonyl chloride (0.078 g, 0.5 mmoles) and pyridine (0.053 g, 0.67 mmoles) and the resulting solution stirred at room temperature for 8 hours.

The solvent was removed and the residue was taken up in EtOAc (110 ml), washed with H$_2$O, 10% KHSO$_4$ solution, brine and dried (Na$_2$SO$_4$). Solvent removal gave a residue that was purified by flash chromatography on silica gel eluting with hexane/EtOAc (75:25) to give pure 1-17 as an oil.

$^1$H NMR (300 MHz, CDCl$_3$) δ0.94 (3H, m) 1.20 (2H, m), 1.36 (3H, m), 1.49 (9H, s), 1.60–1.82 (7H, m), 2.68 (2H, bt), 2.80 (1H, m), 2.95 (4H, m), 3.23 (1H, t), 3.70 (3H, s), 3.92 (2H, m), 4.05 (2H, bd), 4.66 (1H, m), 6.82 (2H, d), 7.07 (2H, d).

EXAMPLE 16

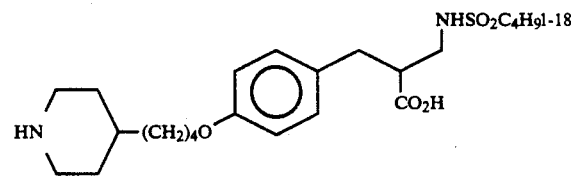

2-[4-(4-Piperindin-4-yl)butyloxy]phenylmethyl-3-(n-butylsulfonylamino)propanoic acid (1-18)

1-17 (0.13 g 0.23 mmoles) was hydrolyzed with LiOH.H$_2$O (0.029 g, 0.69 mmoles) as described for 1-8 to give the desired acid, R$_f$0.3 (silica gel, CHCl$_3$/MeOH/HOAc (97:3:1).

$^1$H NMR (300 MHz, CDCl$_3$) δ0.96 (3H, t) 1.08 (2H, m), 1.22–1.42 (4H, m), 1.46 (9H, s), 1.65 (2H, bd), 1.74 (2H, m), 2.65 (2H, bt), 2.80 (1H, m), 2.96 (4H, m), 3.91 (2H, t), 4.05 (2H, m), 5.51 (1H, t), 6.81 (2H, d), 7.09 (2H, d).

This acid was treated with HCl gas in EtOAc as described for 1-8 to give 1-18 as a white solid, R$_f$0.4 (silica gel, EtOH/NH$_4$OH/H$_2$O (9:1:1).

$^1$H NMR (300 MHz, CD$_3$OD) δ0.96 (3H, t) 1.27–1.58 (9H, m), 1.59–1.80 (6H, m), 1.95 (2H, bd), 2.80 (2H, m), 2.85–3.03 (4H, m), 3.10–3.40 (4H, m), 3.93 (2H, t), 6.80 (2H, d), 7.21 (2H, d).

Compounds useful as fibrinogen receptor antagonists may also be prepared according to the general scheme depicted in Scheme 2. In general terms, a 4-substituted phenolic ester (2-1) is treated with sodium hydride and reacted with an alkyl halide to yield the 1,4-aromatic derivative (2-2). This compound is benzylated to yield 2-3 and deprotected to give the free amine 2-4.

SCHEME 2

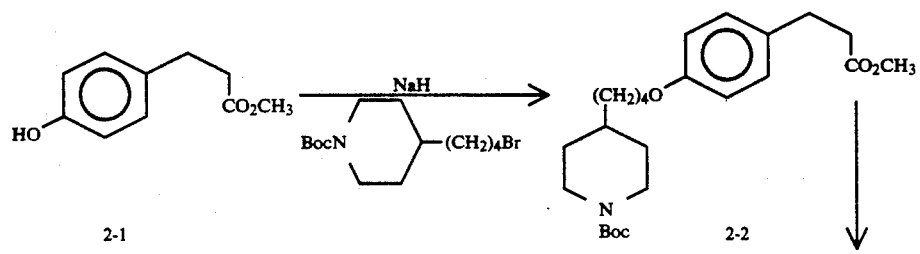

-continued
SCHEME 2

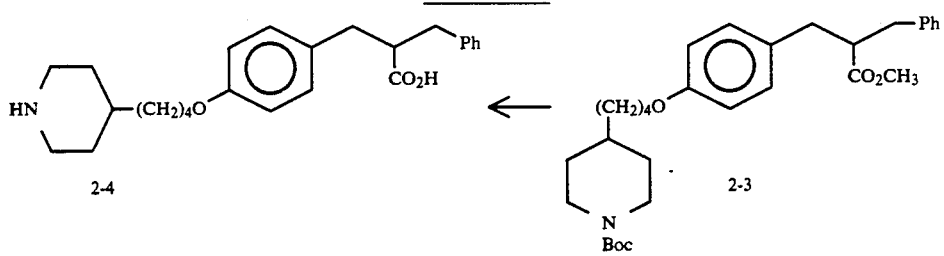

Compounds claimed in the instant invention and depicted in the formula:

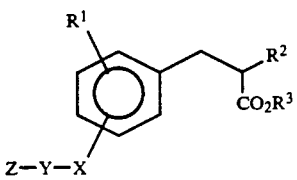

can readily be prepared according to the general procedure described in Scheme 2 by substituting or replacing the various reagents or reactants depending upon the target compound desired.

For example, a trisubstituted 4-substituted phenolic ester may be utilized as the starting reagent in the overall scheme:

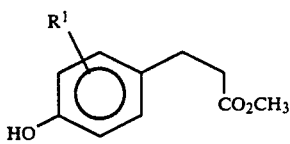

$R^1$ is identical to that described in the Scheme 1 discussion. This compound or the disubstituted derivative may then be reacted with 1-2 or another suitably substituted alkyl halide to yield a compound of the general formula:

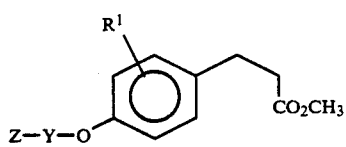

wherein Z-Y-hal is a suitably substituted alkyl halide and Z is chosen from the groups described following the Scheme 1 discussion. The 1,4-substituted aromatic derivatives may then be treated with sodium hydride to produce an enolate which is then reacted with a suitable alkyl halide, arylalkyl halide, activated carbonyl compound (such as dimethylcarbonate) or other suitable electrophilic reagent to yield a compound with the general formula:

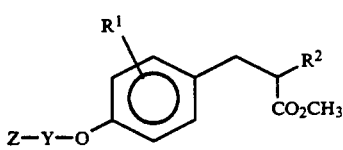

wherein $R^2$ may be hydroxy, aryl$C_{1-10}$alkyl, or $C_{1-6}$ alkyl, wherein the alkyl group is unsubstituted or substituted with amino $C_{1-10}$ alkylcarbonyl or aryl$C_{1-10}$alkylcarbonyl. $R^2$ may also be carboxyl, $C_{1-6}$ alkyloxycarbonyl, $C_{1-6}$ alkylcarbonyl, or $C_{1-10}$ arylalkyl carbonyl.

EXAMPLE 17

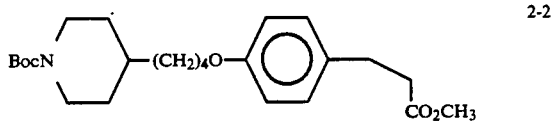

Methyl 3-[4-(4-N-t-Butyloxycarbonylpiperidin-4-yl)butyloxyphenyl]propanoate (2-2)

A solution of methyl 3-(4-hydroxyphenyl)propanoate (2-1) (prepared from the corresponding free acid by treatment with diazomethane) (2.06 g, 0.0114 moles) in DMF (65 ml) was treated with $Cs_2CO_3$ (1.86 g, 0.0057 moles) at room temperature with stirring for 15 minutes. To this was added a solution of 4-(N-t-butyloxycarbonylpiperidin-4-yl)butyl bromide (3.66 g, 0.00114 moles) dropwise at room temperature and this was heated at 75° for 16 hours.

The solvent was removed and the residue taken up in $H_2O$ (100 ml) and extracted with EtOAc. The organic phase was washed with $H_2O$, brine, dried ($Na_2SO_4$) and the solvent removed. The residue was purified by flash chromatography on silica gel eluting with hexane/EtOAc (85:15) to give pure 2-2 as an oil, $R_f$ 0.5.

$^1$H NMR (300 MHz, $CDCl_3$) δ1.08 (2H, m) 1.22–1.41 (4H, m), 1.45 (9H, s), 1.65 (2H, bd), 1.76 (2H, m), 1.74 (2H, m), 2.65 (2H, bt), 2.80 (1H, m), 2.96 (4H, m), 3.91 (2H, t), 4.05 (2H, m), 5.51 (1H, t), 6.81 (2H, d), 7.09 (2H, d).

EXAMPLE 18

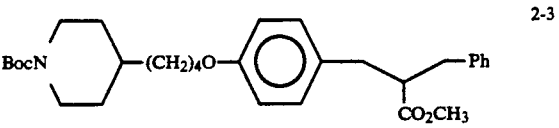

Methyl 3-[4-(4-N-t-Butyloxycarbonylpiperidin-4-yl)butyloxyphenyl]-2-(benzyl)propanoate (2-3)

Diisopropylamine (0.202 g, 2.0 mmoles) in THF (20 ml) was cooled to 0° and treated with n-butyllithium (2.0 mmoles) and the resulting solution stirred at 0° for 0.5 hr. After cooling to −70°, the reaction mixture was treated with 2-2 and stirred for 45 minutes. Then, HMPA (0.18 g, 1.0 mmoles) was added followed by benzyl bromide (0.342 g, 2.0 mmoles) and the reaction mixture was stirred at −70° for 3 hours and then at room temperature for 16 hours.

The reaction was quenched with H₂O (5 ml), the solvent removed and the residue was taken up in EtoAc, washed with 10% KHSO₄ solution, brine and dried (Na₂SO₄). Solvent was removed and the residue purified by flash chromatography on silica gel eluting with hexane/EtOAc (85:15) to give pure 2-3, R_f 0.35.

¹H NMR (300 MHz, CDCl₃) δ1.09 (2H, m), 1.23–7.42 (4H,m), 1.46(9H,s), 1.65(2H,bd), 1.74(2H,m), 2.59–2.82(4H,m), 2.84–3.03(3H,m), 3.47(3H,s), 3.90(2H,t), 4.07(2H,bd), 6.78(2H,d), 7.03(2H,d), 7.05–7.30(5H,m).

EXAMPLE 19

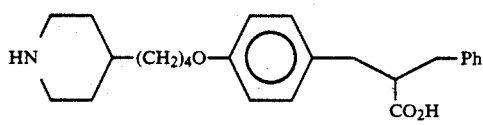

3-[4-(4-Piperidin-4-yl)butyloxyphenyl]-2-(benzyl)-propanoic acid (2-4)

2-3 (0.32 g, 0.628 mmoles) was hydrolyzed with Li-OH.H₂O (0.07 g, 1.88mmoles) as described for 1-8 to give the desired acid, R_f 0.45 (silica gel, •CHCl₃/MeOH/HOAc (97:3:1).

¹H NMR (300 MHz, CDCl₃) δ1.08(2H,m), 1.21–1.40(4H,m), 1.45(9H,s), 1.63(2H,bd), 1.75(2H,m), 2.56–2.81(4H,m), 2.85–3.05(3H,m), 3.90(2H,t), 4.04(2H,m), 6.78(2H,d), 7.06(2H,d), 7.13–7.30(5H,m).

This acid was dissolved in EtOAc and treated with HCl gas as described for 1-8 to give pure 2-4 as a white solid, R_f 0.5 (silica gel, EtOH/NH₄OH/H₂O (9:1:1).

¹H NMR (300 MHz, CD₃OD) δ1.28–1.47(4H,m), 1.48–1.68(3H,m), 1.75(2H,m), 1.95(2H,bd), 2.69–2.80(2H,m), 2.80–3.00(5H,m), 3.35(3H,m), 3.91(2H,t), 6.80(2N,d), 7.07(2H,d), 7.13–7.27(5H,m).

EXAMPLE 20

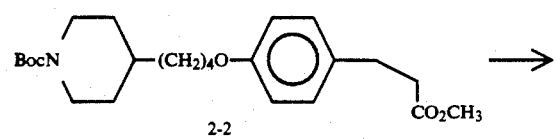

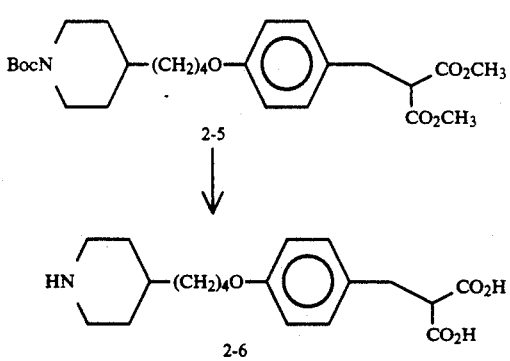

Methyl 2-Carbomethoxy-3-[4-(4-N-t-Butoxycarbonylpiperidin-4-yl)butyloxyphenyl]propanoate (2-5)

A solution of diisopropylamine (0.202 g, 2.0 mmoles) in THF (20 ml) was cooled to 0° and treated with n-butyllithium (2.0 mmoles) followed by stirring for 0.5 hr. This was then cooled to −70° and 2-2 (0.42 g, 1.0 mmoles) in THF (5 ml) was added and the pale yellow solution stirred for 1.0 hr. Then, HMPA (0.179 g, 1.0 mmoles) was added followed by dimethylcarbonate (0.18 g, 2.0 mmoles) and the resulting solution was stirred at −70° for 3 hours and then at room temperature for 12 hours.

The reaction was quenched with H₂O (3 ml) and diluted with EtOAc and 10% KHSO₄ solution, organic phase was washed with 10% KHSO₄ solution, brine, dried (Na₂SO₄) and the solvent removed. The residue was purified by flash chromotography on silica gel eluting with hexane/EtOAc (8:2) to give pure 2-5 as an oil.

¹H NMR (300 MHz, CDCl₃) δ1.10(2H,m), 1.18–1.40(3H,m), 1.47(9H,S), 2.66(2H,d), 2.74(2H,m), 2.68(2H,bt), 3.16(2H,d), 3.64(1H,t), 3.70(3H,S), 3.91(2H,t), 4.08(2H,m), 6.80(2H,d), 7.10(2H,d).

2-Carboxy-3-[4-(4-Piperidin-4-yl)butyloxyphenyl]-propanoic acid (2-6).

2-5 (0.164 g, 0.343 mmoles) was hydrolyzed with LiOH.H₂O (0.072 g, 1.72 mmoles) as described for 1-8 to give the desired acid as an oil.

¹H NMR (300 MHz, CDCl₃) δ1.07 (2H,m), 1.21–1.38(4H,m), 1.45(9H,S), 1.64(2H,d), 1.73(2H,m), 2.62(2H,bd), 3.89(2H,t), 4.03(2H,m), 6.87(2H,d), 7.10(2H,d).

This acid was dissolved in EtOAc and treated with HCl gas as described for 1-9 to give pure 2-6 as a white solid.

¹H NMR (300 MHz, CD₃OD) δ1.28–1.43(4H,m), 1.45–1.70(3H,m), 1.85(2H,m), 1.94(2H,t), 3.07(2H,d), 3.33(2H,m), 3.53(1H,t), 3.92(2H,t), 6.80(2H,d), 7.12(2H,d).

EXAMPLE 21

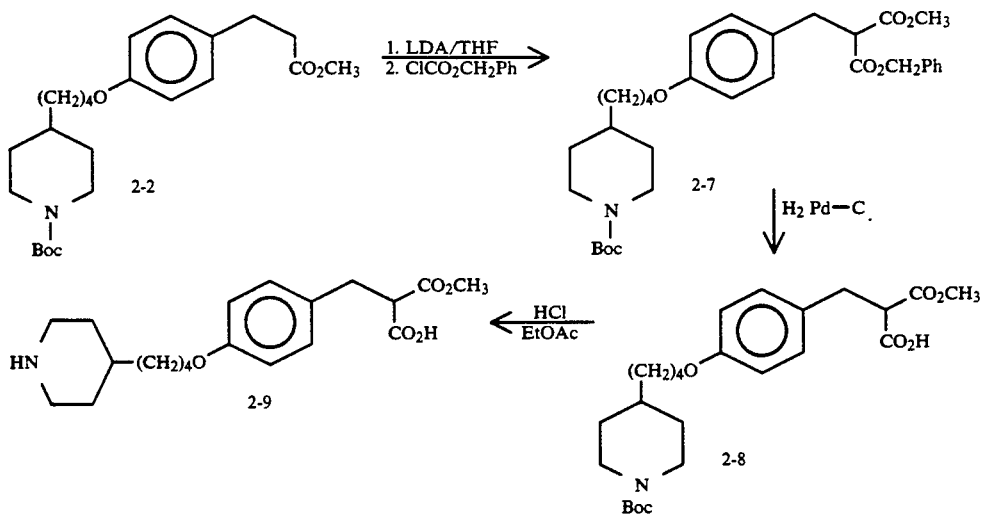

Methyl 2-(Benzyloxycarbonyl)-3-[4-(4-N-t-butyloxycarbonyl-piperidin-4-yl)butyloxyphenyl]propanoate (2-7).

2-2 (0.42 g, 1.0 mmoles) in 5 ml THF was added to a THF solution of lithium diisopropylamide (2.0 mmoles) at 0° with stirring continued for 0.5 hour. This was cooled to −70° and treated with benzyl chloroformate (0.375 g, 2.2 mmoles and the resulting mixture was stirred at −70° for 3 hours and then at room temperature for 12 hours.

The reaction mixture was diluted with 10% KHSO$_4$ solution and extracted with Et$_2$O. The ether phase was washed with 10% KHSO$_4$ solution, brine, dried (Na$_2$SO$_4$) and the solvent removed. The residue was purified by flash chromatography on silica gel eluting with hexane/EtOAc (85:15) to give pure 2-7 as an oil. R$_f$ 0.45, silica gel, hexane/EtOAc (80:20).

$^1$H NMR (300 MHz, CDCl$_3$) δ1.10(2H,m), 1.23–1.42 4H(m), 1.46(9H,S), 1.66(2H,bd), 1.75(2H,m), 2.67(2H,dt), 3.18(2H,d), 3.68(3H,S), 3.80(2H,t), 4.08(2H,bd), 6.86(2H,d), 7.07(2H,d), 7.23(2H,m), 7.34(3H,m)

2-(Carbomethoxy)-3-[4-(4-N-t-butyloxycarbonylpiperidin-4-yl)butyloxyphenyl]propanoic acid (2-8).

2-7(0.301 g) was dissolved in MeOH (30 ml), 100 mg 10% Pd-C was added and this suspension was hydrogenated at atmospheric pressure for 5 hours. The solvent was removed to give 2-8 as an oil.

$^1$H NMR (300 MHz, CDCl$_3$) δ1.08 (2H,m), 1.22–1.40(4H,m), 1.44(9H,S), 1.63(2H, bd), 1.74(2H,m), 2.65(2N,bt), 3.20(2H,d), 3.58(1H,t, 3.62(3H,S), 3.92(2H,t), 4.05(2H,m), 6.80(2H,d), 7.11(2H,d).

2-(Carbomethoxy)-3-[4-(4-piperidin-4-yl)butyloxyphenyl]propanoic acid (2-9).

2-8 (0.25 g) was dissolved in EtOAc and treated with HCl gas as described for 1-9 to give pure 2-9 as a white solid.

$^1$H NMR (300 MHz, CD$_3$OD) δ1.30–1.46(5H,m), 1.48–1.68(2H,m), 1.74(2H,m), 1.95(2H,bd), 2.95(2H,t), 3.08(2H,t), 3.34(3H,m), 3.62(3H,S), 3.91(2H,t), 6.80(2H,d), 7.11(2H,d).

EXAMPLE 22

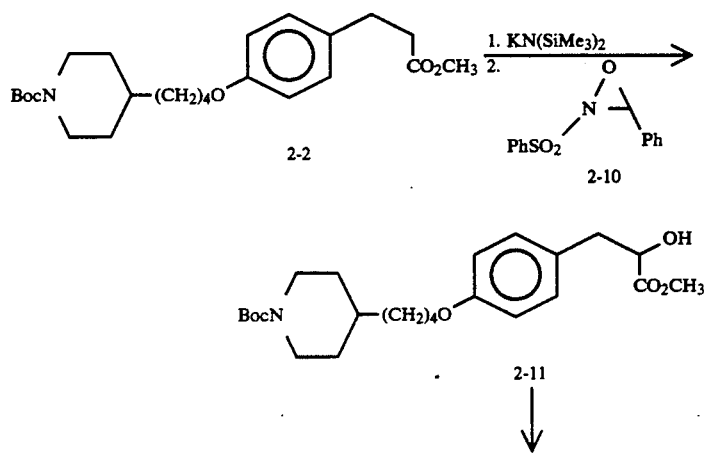

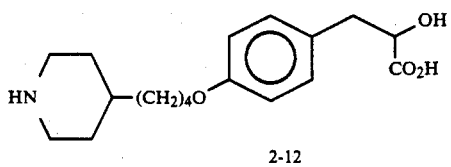

2-12

Methyl 2-Hydroxy-3-[4-(4-N-t-butyloxycarbonylpiperidin-4-yl)butyloxyphenyl]propanoate (2-11)

A solution of 2-2 (0.42 g, 1.0 mmoles) in THF (5 ml) was added to a solution of potassium hexamethyldisilazide (2.0 mmoles) in THF (20 ml) at −70° and this was stirred for 1.0 hour. Then, a solution of oxaziridine 2-10 (0.52 g, 2.0 mmols)* in THF (3 ml) was added at −70° and this was stirred for 4 hours. The reaction was quenched with 10% $KHSO_4$ solution and this was diluted with $Et_2O$ (125 ml). The ether phase was separated, washed with 10% $KHSO_4$ solution, $H_2O$, brine and dried ($Na_2SO_4$). Solvent removal gave a residue that was purified by flash chromatography on silica gel eluting with hexane/EtOAc (7:3), to give pure 2-11.
*J. Org. Chem. 1982, 47, 1775-1777.

$^1$H NMR (300 MHz, $CDCl_3$) δ1.09(2H,m), 1.22–1.41 (4H,m), 1.45(9H,S), 1.65(2H,bd), 1.76(2H,m), 2.67(2H,dt), 2.90(1H,m), 3.05(1H,m), 3.77(3H,S), 3.91(2H,t), 4.08(2H,bd), 4.42(1H,m), 6.81(2H,d), 7.10(2H,d).

2-Hydroxy-3-[4-(4-piperidin-4-yl)butyloxyphenyl]-propanoic acid (2-12).

2-11 (0.31 g, 0.7 mmoles) was hydrolyzed with LiOH.$H_2O$ (0.09 g, 2.14 mmoles) as described for 1-8 to give the desired acid, $R_f$ 0.25 (silica gel, $CHCl_3$/MeOH/HOAc/95:5:1).

$^1$H NMR(300 MHz, $CD_3OD$) δ1.07(2H,m), 1.23–1.39(4H,m), 1.45(9H,S), 1.71(4H,m), 2.72(1H,bt), 2.85(1H,m), 3.09(1H,m), 3.91(1H,t), 4.05(1H,bd), 4.25(1H,m), 6.80(2H,d), 7.18(2H,d).

In addition, compounds of the instant invention which contain two $R^2$ group carbon-carbon bonds may generally be synthesized according to Scheme 3.

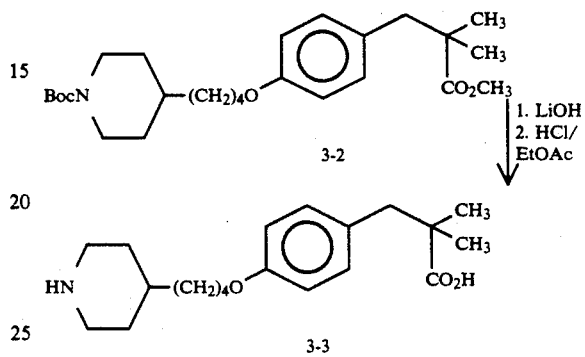

The enolate of 2-2 is alkylated with methyl iodide to provide 3-1 which is isolated. This is then methylated again to give 3-2. Deprotection of the carboxylate and the amine provides the final product 3-3.

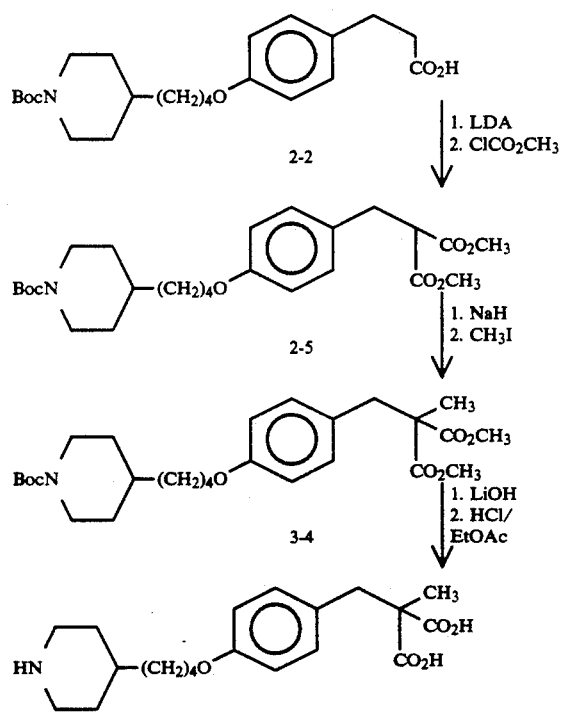

Similarly, intermediate 2-5 is converted to its enolate and then alkylated with methyl iodide or some other suitable agent to give 3-4. Deprotection with base and then acid provides the final product 3-5.

The amino acids used in the instant invention can include but is not limited to the D or L form of the amino acids Alanine, Arginine, Asparagine, Aspartic acid, Cysteine, Glutamic acid, Glutamine, Glycine, Histidine, Isoleucine, Leucine, Lysine, Methionine, Orthithine, Phenylalanine, Proline, Serine, Threonine, Tryptophan, Tyrosine and valine. The D or L form of hydroxylysine, 3-hydroxy-proline, 4-hydroxyproline, allo-isoleucine, allo-hydroxylysine, norvaline, norleucine, $\beta$-methyl proline, $\beta$-$\beta$-demethylproline, $\alpha$-hydroxyproline, anhydroproline, thioproline, $\beta$-methylthioproline or $\beta$-$\beta$-dimethylthioproline. These amino acids may be connected by amide linkages to form polypeptides of two (2) to four (4) amino acids.

Sample alternative protecting groups that can be used in the preparation of the present invention include benzyl ester, cyclohexyl ester, 4-nitrobenzyl ester, t-butyl ester, 4-pyridylmethyl ester, benzyloxycarbonyl, isonicotinyloxycarbonyl, p-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl and 9-fluorenylmethoxycarbonyl.

EXAMPLE 23

In Vitro Activity

The test procedures employed to measure the antiplatelet aggregating activity of the compounds of the present invention are described below.

Blood was drawn into 0.1 volumes of acid citrate-dextrose (85 mM sodium citrate, 64 mM citric acid, 110 mM dextrose) by venipuncture from normal human volunteers. Platelet-rich plasma was prepared by centrifugation at 400× g for 12 minutes. PGE1 (5 mg/ml) was added and platelets were collected by centrifugation at 800× g for 12 minutes. The platelet pellet was resuspended into human platelet buffer (140 mM NaCl, 7.9 mM KCl, 3.3 mM $Na_2HPO_4$, 6 mM HEPES, 2% bovine serum albumin, 0.1% dextrose, pH 7.2) and filtered over Sepharose 2B that was previously equilibrated in human platelet buffer. Human fibrinogen (10–100 mg/ml) and Ca $Cl_2$ (1 mM) were added and aggregation was initiated by the addition of 10 mM ADP. Aggregation was monitored by the initial rate of increase of light transmittance.

The $IC_{50}$ (uM) of a number of compounds claimed in the instant invention are described below in Table 1. This table demonstrates the relative inhibitory effects depending upon the various $R^2$ substituents on the compound of the general formula:

TABLE 1

| $R^2$ | $IC_{50}$ (uM) |
|---|---|
| $CH_2SO_2CH_2Ph$ | 1.6 |
| $CH_2NHC(O)Ph$ | 3.1 |
| $CH_2Ph$ | 115.0 |
| $CH_2NHSO_2C_4H_9$ | 2.9 |
| $CO_2CH_3$ | 5.8 |
| OH | 8.6 |
| $CO_2H$ | 3.2 |
| $CH_2NHCH_2Ph$ | 18.0 |
| $CH_2SO_2C_4H_9$ | 0.65 |

Therapeutic Treatment

Compounds of the invention may be used for inhibiting integrin protein-complex function relating to cell attachment activity. They may be administered to patients where inhibition of human or mammalian platelet aggregation or adhesion is desired.

Compounds of the invention are eliminated from circulation rapidly and are particularly useful in inhibiting platelet aggregation in situations where a strong antithrombotic of short duration or effectiveness is needed. Thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporael circuit. Adhesion is dependent on the interaction between GPIIb-/IIIa on the platelet membranes and fibrinogen adsorbed to the surface of the circuit. (Lluszko et al., Amer. J. Physiol., 252:H, 615–621 (1987). Platelets released from artificial surfaces show impaired hemostatic function. Compounds of the invention may be administered to prevent adhesion.

Other applications of these compounds include prevention of platelet thrombosis, thromboembolism and reocclusion during and after thromboembolytic therapy and prevention of platelet thrombosis, thromboembolism and reocclusion after angioplasty of coronary and other arteries and after coronary artery bypass procedures. Compounds of the invention may also be used to prevent myocardial infarction.

These compounds may be administered by any convenient means which will result in its delivery into the blood stream in substantial amount including continuous intravenous or bolus injection or oral methods. Compositions of the invention include compounds of the invention and pharmaceutically acceptable carriers, e.g. saline, at a pH level of for example 7.4, suitable for achieving inhibition of platelet aggregation. They may also be used in combination with anticoagulants such as heparin or warfarin. Intravenous administration is presently comtemplated as the preferred administration route. They are soluble in water.

In one exemplary application, a suitable amount of compound is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.01–30 uM, preferably between about 0.03–3 uM. When this amount is achieved, an infusion of between about 0.1–100 mg per kilo per min., preferably between about 1–20 mg per kilo per min. is maintained to inhibit platelet aggregation. Should the patient need to undergo bypass surgery, administration may be stopped immediately and will not cause complications during surgery that would be caused by other materials such as aspirin or monoclonal antibodies, the effects of which last hours after cessation of administration.

The present invention also includes a pharmaceutical composition comprising compounds of the present invention and tissue type plasminogen activitor or streptokinase. The invention also includes a method for promoting thrombolysis and preventing reocclusion in a patient which comprises administering to the patient an effective amount of compositions of the invention.

The present invention may be embodied in other specific forms without departing from the spirt or essential attributes thereof. Thus, the specific examples described above should not be interpreted as limiting the scope of the present invention.

While the invention has been described and illustrated in reference to certain preferred embodiments thereof, those skilled in the art will appreciate that various changes, modification and substitutions can be made therein without departing from the spirt and the scope of the invention. For example, effective dosages other than the preferred doses as set fourth hereinabove may be applicable as a consequence of variations in the responsiveness of the mammal being treating for severity of clotting disorders or emboli, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The following compounds are further illustrative of the scope of the present invention:

TABLE 2

| $R^1$ | Z | Y | X | $R^2$ | $R^3$ |
|---|---|---|---|---|---|
| H | piperidinyl (HN) | $(CH_2)_3$ | NHCO | $CH_2NHCCH_3$ (with C=O) | H |
| $-OCH_2CO_2H$ | $H_2N-$ | $(CH_2)_2$-cyclohexyl-$CH_2$ | O | $OCH_2Ph$ | $CH_3$ |
| $CH_2CH_3$ | $H_2NC(=NH)-$ | $CH_2-N$(C=O)$N-$ (imidazolidinone) | $CH_2$ | $CH_2SO_2Ph$ | $C_2H_5$ |
| $-OCH_2CH_3$ | $H_2N-C(=NH)-NH-$ | $-(CH_2)_2O(CH_2)-$ | CO | F | H |
| Cl | $CH_2CH_2OCH_3$, N-Ph | $-(CH_2)_6-$ | CONH | $CH_2-C(=O)-CH_2-$furanyl | H |
| $CH_3NHCH_2$ | piperidinyl-NH-C(=NH)H | $-CH(CH_3)-$cyclohexyl | $NHSO_2$ | $CH_2C(=O)NH-CH(CH_3)-CO_2H$ | $CH_3$ |
| $CH_3SO_2CH_2$ | azabicyclic | $-CH_2-$thiophene$-C(=O)-$ | $-CH=CH_2-$ | $CH_2NHSO_2CH_2CH_3$ | $C_2H_5$ |
| $-CH_2CO_2H$ | $CH_3NHC(=NH)NH-$ | piperidinone ($CH_2$, N-, C=O) | $CH_2$ | $-CH_2SO_2NH-CH(CH_2Ph)-C(=O)NH-CH(CH_3)-CO_2H$ | H |

TABLE 2-continued

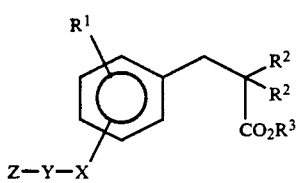

| R¹ | Z | Y | X | R² | R³ |
|---|---|---|---|---|---|
| F | HN⟨pyrrolidine⟩ | (CH$_2$)$_5$ | O | CH$_2$OCH$_3$ | H |

What is claimed is:

1. A compound of the formula:

and the pharmaceutically acceptable salts thereof, wherein $R^1$ is chosen from
- H,
- $C_{1-6}$ alkyl,
- phenyl$C_{1-10}$alkyl,
- phenyl,
- carboxy,
- $C_{1-6}$ alkyloxy,
- carboxy$C_{0-6}$alkyl,
- carboxy$C_{0-6}$alkyloxy,
- hydroxy$C_{0-6}$alkyl,
- $C_{1-4}$ alkylsulfonyl$C_{0-6}$alkyl,
- $C_{0-4}$ alkylamino$C_{0-6}$alkyl,
- $C_{0-10}$ phenylalkylamino$C_{0-6}$alkyl,
- $C_{2-10}$ acylamino$C_{0-6}$alkyl,
- $C_{1-4}$ carboalkoxy$C_{0-6}$alkyl, or
- halogen;

$R^2$ is independently
- H,
- halogen,
- hydroxy,
- $C_{1-6}$ alkyloxy,
- phenyl$C_{0-4}$alkyl,
- phenyl$C_{0-6}$alkyloxy,
- $C_{1-6}$ alkyl, wherein the alkyl group is unsubstituted or substituted with one or more groups chosen from: hydroxy, $C_{1-4}$ alkyloxy, amino$C_{1-10}$alkylcarbonyl, phenyl $C_{0-10}$alkylcarbonyl, $C_{1-6}$ alkylcarbonyl amino, phenyl$C_{0-6}$alkylcarbonylamino, $C_{1-6}$ alkylsulfonyl, $C_{1-6}$ alkylthio, phenyl$C_{0-10}$ alkylsulfonyl, phenyl$C_{1-6}$alkylthio, $C_{1-6}$alkylsulfonylamino, phenyl$C_{0-10}$ alkylsulfonylamino, $C_{1-10}$alkyloxy carbonylamino, phenyl$C_{0-6}$ alkylamino, phenyl$C_{0-6}$alkyl carbonylamino, amino, carboxyl, phenyl,;
- carboxyl,
- $C_{1-6}$ alkylcarbonyl,
- phenyl$C_{0-10}$alkylcarbonyl,
- $C_{1-6}$alkyloxycarbonylamino$C_{1-6}$alkyl,
- $C_{0-6}$alkylaminocarbonylamino$C_{1-6}$alkyl,
- $C_{1-6}$ alkyloxycarbonyl, or
- phenyl$C_{0-6}$alkyloxycarbonylamino $C_{1-6}$alkyl;

$R^3$ is
- H,
- $C_{1-6}$ alkyl, or
- phenyl$C_{1-10}$alkyl;

Z is
- a 6-membered monocyclic saturated ring system containing one nitrogen as the single heteroatom and either unsubstituted or substituted with $R^4$ or $R^5$ wherein $R^4$ and $R^5$ are independently H, $C_{1-6}$ alkyl, or phenyl $C_{1-10}$ alkyl wherein said alkyl groups are unsubstituted or substituted with $C_{1-4}$alkyloxy, carboxy $C_{0-6}$ alkyl, hydroxy, or halogen;

Y is
- -$C_{1-10}$ alkyl- either unsubstituted or substituted with one or more groups selected from $R^4$ or $R^5$;
- -$C_{4-8}$ cycloalkyl-, -phenyl-,
- -$C_{0-3}$alkyl phenyl$C_{0-3}$alkyl-,
- -$C_{0-3}$alkyl phenyl$C_{0-3}$alkylcarbonyl-,
- -$C_{0-3}$ alkyl phenyl$C_{0-3}$alkylcarboxamido-,
- -$C_{0-3}$ alkyl phenyloxy$C_{0-3}$alkyl-,
- -$C_{0-3}$alkyloxy$C_{0-6}$alkyl-, $$-\overset{O}{\underset{\|}{C}}-NH-, \text{ or } -NH-\overset{O}{\underset{\|}{C}}-;$$

X is
- —O—,
- —S—,
- —SO—,
- —SO$_2$—,
- —CO—,
- —NR$^4$CO—,
- —CONR$^4$—,
- —CH$_2$—,
- —CH=CH—,
- —C≡C—,
- —NR$^4$CS—,
- —CSNR$^4$—,
- —SO$_2$NR$^4$—, or
- —NR$^4$SO$_2$—.

2. A compound according to claim 1 wherein said compound is:

Methyl 3-[4-(4-N-t-Butyloxycarbonylpiperdin-4-yl)-butyloxyphenyl]-2-(benzyl)propanoate; or 3-[4-(4-Piperidin-4-yl)butyloxyphenyl]-2-(benzyl)-propanoic acid; or Methyl 2-carbomethoxy-3-[4-(4-N-t-butyloxycarbonyl-piperidin-4-yl)butyloxyphenyl]propanoate; or 2-Carboxy-3-[4-(4-Piperidin-4-yl)butyloxyphenyl]-propanoic acid; or Methyl 2-(Benzyloxycarbonyl)-3-[4-(4-N-t-butyloxycarbonylpiperidin-4-yl)butyloxyphenyl]propanoate; or 2-(Carbomethoxy)-3-[4-(4-N-t-butyloxycarbonylpiperidin-4-yl)butyloxyphenyl]propanoic acid; or 2-(Carbomethoxy)-3-[4-(4-piperidin-4-yl)butyloxyphenyl]propanoic acid; or Methyl 3-[4-(4-N-t-butyloxycarbonylpiperidin-4-yl)butyloxyphenyl]propanoate; or Methyl 2-Hydroxy-3-[4-(4-N-t-butyloxycarbonylpiperidin-4-yl)butyloxyphenyl]propanoate; or 2-Hydroxy-3-[4-(4-piperidin-4-yl)butyloxyphenyl]propanoic acid.

3. A compound according to claim 1 wherein said compound is:

Methyl 2-[4-(4-N-t-Butyloxycarbonylpiperidin-4-yl)butyloxy]phenylmethyl-3-(n-butylthio)propanoate; or Methyl 2-[4-(4-N-t-Butyloxycarbonylpiperidin-4-yl)butyloxy]phenylmethyl-3-(n-butylsulfonyl)propanoate; or 2-[4-(4-Piperidin-4-yl)butyloxy]phenylmethyl-3-(n-butylsulfonyl)propanoic acid; or Methyl 2-[4-(4-N-t-Butyloxycarbonylpiperidin-4-yl)butyloxy]phenylmethyl-3-(benzylthio)propanoate; or Methyl 2-[4-(4-piperidin-4-yl)-butyloxy]phenylmethyl-3-(benzylsulfonyl)propanoate; or 2-[4-(Piperidin-4-yl)butyloxy]phenylmethyl-3-(benzylsulfonyl)propanoic acid; or Methyl 2-[4-(4-N-t-Butyloxycarbonylpiperidin-4-yl)butyloxy]phenylmethyl-3-(benzylamino)propanoate; or 2-[4-(Piperidin-4-yl)butyloxy]phenylmethyl-3-(benzylamino)propanoic acid; or Methyl 2-[4-(4-N-t-Butyloxycarbonylpiperidin-4-yl)butyloxy]phenylmethyl-3-(amino)propanoate; or Methyl 2-[4-(4-N-t-Butyloxycarbonylpiperidin-4-yl)butyloxy]phenylmethyl-3-(benzoylamino)propanoate; or 2-[4-(Piperidin-4-yl)butyloxy]phenylmethyl-3-(benzoylamino)propanoic acid; or Methyl 2-[4-(4-N-t-Butyloxycarbonylpiperidin-4-yl)butyloxy]phenylmethyl-3-(n-butylsulfonylamino)propanoic acid, or 2-[4-(Piperidin-4-yl)butyloxy]phenylmethyl-3-(n-butylsulfonylamino)propanoic acid.

4. A method of blocking fibrinogen from acting at its receptor site in a mammal, including a human comprising administering a pharmacologically effective amount of a compound as claimed in claim 1.

5. A method of preventing thrombus and embolus formation in a mammal, including a human, in need thereof, comprising administering a pharmacologically effective amount of a compound as claimed in claim 1.

6. A method of treating thrombus and embolus formation in a mammal, including a human, in need thereof, comprising administering a pharmacologically effective amount of a compound as claimed in claim 1.

7. A method of inhibiting aggregation of blood platelets in a mammal, including a human, comprising administering a pharmacologically effective amount of a compound as claimed in claim 1.

8. A pharmaceutical composiiton, comprising a compound as claimed in claim 1, and a pharmaceutically acceptable carrier.

9. The composition as claimed in claim 8, in which said pharmaceutically acceptable carrier consists of a sustained release pharmaceutical formulation.

10. A pharmaceutical composition for inhibiting the binding of fibrinogen to blood platelets in a mammal, including a human, comprising a compound of claim 1 and a pharmaceutically acceptable carrier.

11. A pharmaceutical composition for inhibiting the aggregation of blood platelets in a mammal, including a human, comprising a compound of claim 1 and a pharmaceutically acceptable carrier.

12. A composition for preventing thrombus or embolus formation in a mammal, including a human, pharmaceutically acceptable carrier.

13. A composition for treating thrombus or embolus formation in a mammal, including a human, comprising a compound of claim 1 and a pharmaceutically acceptable carrier.

14. A method for inhibiting the aggregation of blood platelets in a mammal, including a human, comprising administering the composition of claim 8.

15. A method for preventing or treating thrombus or embolus formation in a mammal, comprising administering the composition of claim 9.

* * * * *